United States Patent [19]

Slough

[11] Patent Number: 4,718,774
[45] Date of Patent: Jan. 12, 1988

[54] SCALE MONITORING MEANS AND METHOD

[75] Inventor: Carlton M. Slough, Spring, Tex.

[73] Assignee: Texaco Inc., White Plains, N.Y.

[21] Appl. No.: 855,038

[22] Filed: Apr. 23, 1986

[51] Int. Cl.$^4$ ............................................. G01N 25/44
[52] U.S. Cl. ............................................ 374/7; 374/33; 374/45
[58] Field of Search ................. 374/45, 7, 33; 165/32; 204/404

[56] References Cited

U.S. PATENT DOCUMENTS

| | | | |
|---|---|---|---|
| 3,913,378 | 10/1975 | Hausler | 374/7 |
| 4,098,662 | 7/1978 | Schell et al. | 374/7 |
| 4,383,438 | 5/1983 | Eaton | 374/7 X |

Primary Examiner—Daniel M. Yasich
Attorney, Agent, or Firm—Robert A. Kulason; James J. O'Loughlin; Ronald G. Gillespie

[57] ABSTRACT

The present invention is a system and method for determining the onset of scale in a pipeline carrying a petroleum liquid. A source provides electrical energy to a heating element in a housing adapted to fit in the pipeline. The housing also encloses a sensor for sensing the temperature of the petroleum liquid and providing a corresponding electrical signal. The housing is arranged with the heating element and the sensor in such a manner that there is heat transfer to and from the petroleum liquid so that as scale starts to coat the housing it affects the transfer of heat.

9 Claims, 1 Drawing Figure

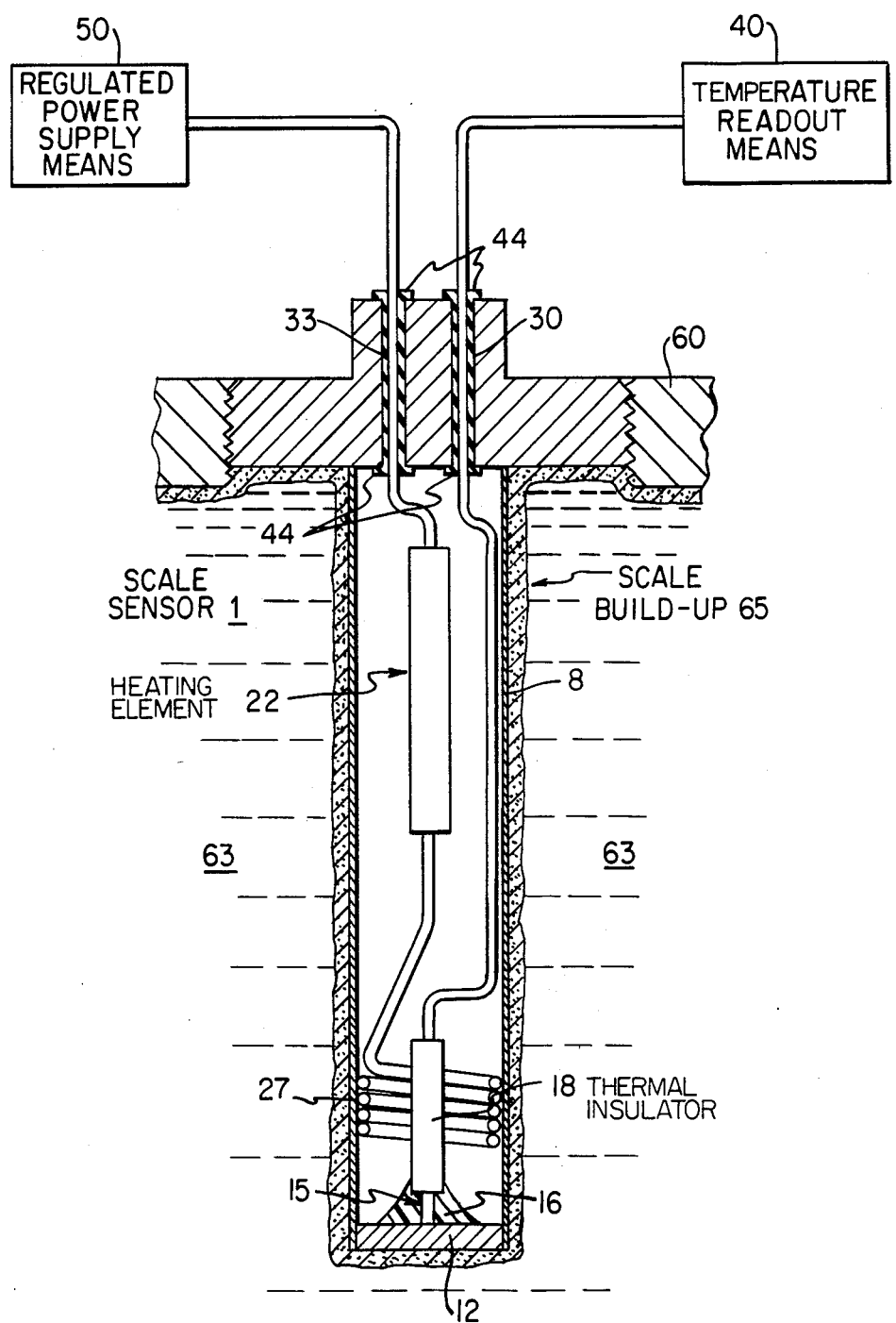

SCALE MONITORING MEANS AND METHOD

BACKGROUND OF THE INVENTION

Field of the Invention

The present invention relates to a monitor and monitoring method for determining the onset of scale in a pipeline carrying a petroleum liquid.

SUMMARY OF THE INVENTION

The present invention is a system and method for determining the onset of scale in a pipeline carrying a petroleum liquid. A source provides electrical energy to a heating element in a housing adapted to fit in the pipeline. The housing also encloses a sensor for sensing the temperature of the petroleum liquid and providing a corresponding electrical signal. The housing is arranged with the heating element and the sensor in such a manner that there is heat transfer to and from the petroleum liquid so that as scale starts to coat the housing it affects the transfer of heat.

The objects and advantages of the invention will appear more fully hereinafter from a consideration of the detailed description which follows, taken together with the accompanying drawing, wherein one embodiment of the invention is illustrated by way of example. It is to be expressly understood, however, that the drawing is for illustration purposes only, and is not to be construed as defining the limits of the invention.

DESCRIPTION OF THE DRAWING

The drawing is a part simplified block diagram and part assembly type diagram of a scale monitor constructed in accordance with the present invention.

DESCRIPTION OF THE INVENTION

With reference to the drawing, there is shown a scale sensor 1 having a standard pipe plug 5 modified as hereinafter explained. Attached to plug 5 is a tube 8 whose unattached end is closed with a heat conductive end plate 12. A heat sensor 15, which may be of the type AD 590, manufactured by Analog Devices, is maintained in contact with end plate 12 with a silicon rubber 16. Heat sensor 15 is substantially covered with thermal insulator 18.

Also located within scale sensor 1 is a heating element 22 of the type Wall-25W, manufactured by Lenk-Wall Inc. Heating element 22 is thermally connected to a heat transfer coil 27, which is in contact with the cylinder 8.

Pipe plug 5 has two holes 30 and 33. Wires connect heat sensor 15 with temperature read-out means 40 which pass through hole 30 and pipe plug 5. Hole 30 is hermetically sealed with seals 44 at each end. Wires connected to heating element 22 pass through hole 33 and are connected to a regulator power supply 50. Again hole 33 has hermetic seals 44 at each end.

Scale sensor 1 may be inserted in a pipeline 60 carrying a petroleum stream 63. Regulator power supply means provides d.c. voltage to heating element 22 causing it to provide heat. In turn, heating element 22 causes heat to pass from scale sensor 1 into the petroleum stream carried in the pipeline, causing the surrounding area to heat a few degrees above that of the normal stream temperature. The heat input can be done as a fixed quantity or steady state (fixed rate) or pulsed. The temperature sensor 15 senses the temperature and provides a corresponding signal back to temperature readout means 40. All the elements of temperature readout means 40 are well known in the art. As a scale build-up 65 occurs on scale sensor 1 it affects the temperature being sensed by temperature sensor 15, or to put it another way the heat transfer from scale sensor 1 will be different for a coated scale sensor 1 and a clean (uncoated) scale sensor 1. This difference can be determined from the measurements of temperature readout means 40 and used to determine onset of scaling.

The method of using the present invention may be as follows.

The temperature of fluids produced from an oil well is largely determined by conditions existing in the producing formation and will be stable over long periods of time. This allows the temperature of the produced fluids to be used as a base line or reference temperature. The fact that different wells in different locations may have different temperatures, does not pose a problem as will be seen. In making determinations for scale formation, a clean (uncoated) scale sensor 1 is immersed in petroleum stream 63 and allowed to come to temperature equilibrium. This temperature in measured by the heat sensor 15 and may be noted as being temperature T1. In the next step, clean scale sensor 1 has its heating element 22 energized in a predetermined manner. The clean probe temperature will rise a few degrees above the petroleum stream 63 temperature (T1). When the scale sensor 1 reaches equilibrium while applying heat, the temperature is noted as T2.

These two temperatures, T1 and T2, define the unheated and heated equilibrium temperatures for a given petroleum stream and should be stable and repeatable over a reasonably long period (months). The aforementioned steps are repeated at suitable intervals, such as daily, weekly, or monthly. As long as temperatures T1 and T2 repeat, no scale is forming. However, should scale form on scale sensor 1 it will interfere with the transfer of heat between scale sensor 1 and petroleum stream 63 during the heated measurement, and T2 will be higher. T1 should remain the same. This condition signals the operator to take corrective action, and it should be noted as the onset of scale.

Although the previous example has shown the operation of the present invention in a pipeline carrying a petroleum stream, it may also be used in the laboratory. Obviously, pipe plug 5 may be replaced with some kind of an end cap that will allow the passage of the wires from heat sensor 15 and heating element 22 to their respective outside equipment.

What is claimed is:

1. A system for determining the onset of scale in a pipeline carrying a petroleum liquid stream comprising:
   means for providing electrical energy;
   housing means mounted in said pipeline for affecting the transfer of heat to and from the petroleum liquid stream as a function of scale forming on the housing means, said housing means includes:
   heating means connected to the electrical means for periodically providing heat in accordance with the received electrical energy,
   first heat transfer means for transferring heat from the heating means to the petroleum stream,
   sensing means for sensing temperature before each providing of heat and after each providing of heat,
   second heat transfer means for transferring heat from the petroleum stream to the sensing means so that the sensing means is sensing the temperature of the petroleum stream; and monitor means connected to the sensing means in the housing means for providing an indication of the temperatures sensed by the sensing means so as to provide an indication of the onset of scale in the pipeline.

2. A system as described in claim 1 in which the housing means includes:

end plug sensor means for maintaining said scale means in said pipeline and said end plug means having holes therein for the passage of wires, wires, which pass through said end plug means and connect the heating means to the electrical energy means and the sensing means to the monitor means, sealing means for sealing said wires in the holes in said end plug means, a heat conductive tube affixed to said end plug means and enclosing the heating means and the sensing means transfers heat from the heating means to the petroleum liquid stream, and end plate means affixed to the end of the tube for transferring heat from the petroleum liquid stream to the sensing means.

3. A system as described in claim 2 in which the heating means includes:

a heating element responsive to electric energy from the electrical energy means for providing heat, and a coil of tubing affixed to the heating element and making contact with the tube so as to provide heat from the heating element to the tube for transfer into the petroleum liquid stream.

4. A system as described in claim 3 in which the sensing means includes:

a heat sensor in contact with the end plate means, and heat insulating material surrounding said heat sensor to prevent the heat from the heating means from affecting the heat sensor.

5. A method for determining the onset of scale in a pipeline carrying a petroleum liquid stream comprising the steps of:

a. inserting a housing into the petroleum stream,
b. sensing the temperature of the petroleum stream with a temperature sensor,
c. displaying the sensed temperature,
d. heating the petroleum stream with a heating element and heat transfer coil located within the housing,
e. sensing the temperature of the petroleum stream with the temperature sensor when an equilibrium condition has been reached,
f. displaying the equilibrium condition temperature,
g. stopping the heating of the petroleum stream,
h. repeating steps b through g periodically, and
i. determining the onset of scale in the pipeline from the displayed temperatures.

6. Apparatus for determining the onset of scale in a pipeline carrying a petroleum liquid comprising:

means for providing electrical energy, heating means responsive to the electrical energy for periodically providing heat to the petroleum liquid in accordance with received electrical energy, sensing means for sensing the temperature of the petroleum liquid prior to the each providing of heat to the petroleum stream and after each providing of heat to the petroleum stream and providing a corresponding electrical signal, housing means enclosing the heat means and the temperature sensing means for effecting the transfer of heat to and from the petroleum liquid as a function of scale forming on the housing means, and monitor means connected to the sensing means for providing an indication of the sensed temperatures in accordance with the signal from the sensing means so as to provide an indication of the onset of scale in the pipeline.

7. A system as described in claim 6 in which the housing means includes:

end plug having holes therein for the passage of wires, wires, which pass through said end plug and connect the heating means to the electrical energy means and the sensing means to the monitor means, sealing means for sealing said wires in the holes in said end plug, a heat conductive tube, affixed to said end plug and enclosing the heating means and the sensing means transfers heat from the heating means to the petroleum liquid, and end plate means affixed to the end of the tube for transferring heat from the petroleum liquid to the sensing means.

8. Apparatus as described in claim 7 in which the heating means includes:

a heating element responsive to electric energy from the electrical energy means for providing heat, and a coil of tubing affixed to the heating element and making contact with the tube so as to provide heat from the heating element to the tube for transfer into the petroleum liquid.

9. A system as described in claim 8 in which the sensing means includes:

a heat sensor in contact with the end plate means, and heat insulating material surrounding said heat sensor to prevent the heat from the heating means from affecting the heat sensor.

* * * * *